United States Patent [19]

McBride, Jr.

[11] 4,253,064
[45] Feb. 24, 1981

[54] LIQUID LEVEL SENSING SYSTEM

[75] Inventor: Lyle E. McBride, Jr., Norton, Mass.

[73] Assignee: Texas Instruments Incorporated, Attleboro, Mass.

[21] Appl. No.: 912,132

[22] Filed: Jun. 2, 1978

[51] Int. Cl.³ ........................................... G01N 27/42
[52] U.S. Cl. ..................................... 324/436; 331/65; 324/65 CR
[58] Field of Search ...................... 324/29, 30 R, 30 A, 324/30 B, 65 CR, 436; 331/65

[56] References Cited

U.S. PATENT DOCUMENTS

| | | | |
|---|---|---|---|
| 3,254,333 | 5/1966 | Baumoel | 331/65 |
| 3,340,866 | 9/1967 | Noller | 324/30 R |
| 3,805,184 | 4/1974 | Visioli | 331/65 |
| 3,906,353 | 9/1975 | Murdock | 324/30 R |
| 4,101,828 | 7/1978 | Dehler | 324/65 CR |

*Primary Examiner*—Michael J. Tokar
*Attorney, Agent, or Firm*—John A. Haug; James P. McAndrews; Melvin Sharp

[57] ABSTRACT

A system for determining the presence or absence of coolant liquid as well as for monitoring the effectiveness of corrosion inhibition of the liquid includes a high impedance differential amplifier to which two electrodes, adapted to be immersed in the liquid, are connected. The high impedance differential amplifier measures the d.c. potential of the electrodes as an indication of the effectiveness of the corrosion inhibition characteristic of the liquid. The output of the amplifier is connected to a detector which in turn is connected to conventional indication means such as a light emitting diode. A conventional power source provides positive and negative power to the amplifier. The output of the amplifier is also connected to one of its two inputs through a feedback network comprising a capacitor and a resistance which includes the resistance between the electrodes. An electrically insulative barrier may be interposed between the electrodes or one of the electrodes may be grounded through a relatively large capacitor. The amplifier-feedback network can be used to determine the presence or absence of liquid independently of the corrosion monitoring function if desired.

10 Claims, 3 Drawing Figures

LIQUID LEVEL SENSING SYSTEM

BACKGROUND OF THE INVENTION

1. Field of the Invention

This invention relates to a system for sensing the presence or absence of a liquid and more particularly to the adaptation of a system which is used to monitor the effectiveness of the corrosion inhibition character of a vehicular coolant liquid to additionally sense the presence or absence of such liquid without deleteriously effecting its monitoring performance.

2. Description of the Prior Art

A great deal of effort is expended throughout industry in an attempt to prevent, or at least mitigate, corrosion of metal components. In the automotive industry, for instance, among the various preventive measures that are commonly taken is the use of additives in vehicular coolant systems to inhibit corrosion. Commerically available permanent antifreeze used in automotive cooling systems inhibits corrosion of the radiator and allied metallic components until it chemically breaks down with age, is diluted with water or is contaminated in some way. Recently systems have been developed to monitor the effectiveness of the corrosion inhibition characteristic of such coolant material whereby visual indication is provided upon the loss of this characteristic so that the coolant liquid can be replaced before any corrosion occurs but not before replacement is required. Examples of such systems are found in copending applications Ser. No. 879,188 filed Feb. 21, 1978 and Ser. No. 866,074 filed Dec. 30, 1977, both assigned to the assignee of the present invention. In these systems a potential measuring circuit employing at least two electrochemical electrodes composed of dissimilar metals are located so as to be immersed and in contact with coolant liquid. When the inhibiting characteristic is effective a first range of electrical potential exists between the electrodes; however, when the inhibiting characteristic becomes ineffective for any reason, a second range of electrical potential exists therebetween. Upon reaching a threshold level, as the potential moves into the second range, indicating means are activated to provide suitable indication of the condition. For instance a light mounted in the dashboard can be actuated when the coolant liquid becomes corrosive.

In addition to systems for monitoring the effectiveness of the inhibition characteristics of coolant liquid it would also be advantageous to provide means for indicating whether an adequate supply of coolant liquid exists in the cooling system to perform its intended cooling function. A common way to provide this type of information is to mount a liquid level sensor at a selected position in the cooling system so that when the sensor is inundated it is in a first operating mode and when it is not so inundated it is in a second operating mode. Thus when the liquid level drops below the sensor and the sensor goes into its second operating mode, an alarm is given indicating the existance of an inadequate supply of coolant liquid.

However, if the monitoring systems of the above mentioned applications are employed, then a sensor is already disposed in the cooling system so it would be very desirable to use this same sensor to provide the level sensing function as well as the function of monitoring the effectiveness of the corrosion inhibition characteristic of the fluid. Given the existence of a sensor comprising one or more electrodes a conventional approach for sensing the presence or absence of an electrically conductive liquid would entail passing current between an electrode and ground so that the potential measured between the electrode and ground would serve to indicate the presence or absence of liquid. In such systems, in order to avoid false tripping due to noise a reasonably large trip potential is desirable, for example, in the order of one volt. However, to avoid false high level indication due to leakage through liquid clinging to the insulator header mounting the electrode, a reasonably low trip resistance is necessary, for example, in the order of 5000-10,000 ohms. One volt at 10,000 ohms results in 100 microamperes of current which, if used with the monitoring system set forth in the aforementioned applications, would not be acceptable due to polarization it would cause. Even where a separate level sensor is employed, that is independently of the corrosion sensing function, such current levels can cause unacceptable electrolytic reactions. It has been found that for use with the above referenced corrosion sensor systems, as little as one microampere produces unacceptable polarization.

SUMMARY OF THE INVENTION

The present invention provides means to indicate the presence or absence of liquid without passing any appreciable current through the liquid when present, permitting the utilization of structure intended for a different function without adversely affecting that function. Briefly, the invention makes use of the electrical resistance between two electrodes as part of a feedback network in a feedback oscillator. The feedback oscillator may incorporate a d.c. measuring amplifier for measuring the electrode potential as an indication of the corrosion inhibition characteristic of liquid in which the electrodes are immersed. This same amplifier provides the amplification necessary for oscillation when the resistance between the electrodes increases to a threshold level indicating an absence of liquid. The feedback network includes a capacitor which not only determines the frequency of oscillation, along with appropriate resistance, but also blocks any possible d.c. current which otherwise might flow through the electrodes. The sensing of liquid presence/absence is accomplished between a first electrode and ground while a second electrode may be directly grounded, coupled to ground through a large capacitor or resistor or is separated from the first electrode by an electrically insulative barrier and thus coupled to ground through the liquid clinging to the insulator separating said second electrode from ground.

Thus it is an object of the invention to provide a sensor which indicates the presence or absence of an adequate supply of coolant liquid in a cooling system. Another object is the provision of a system which in addition to monitoring the effectiveness of the corrosion inhibition characteristic of a liquid also determines whether there is an adequate supply of such liquid to perform its cooling function. Yet another object is the provision of means to sense the level of liquid using electrodes which are used in a system for d.c. potential measurement without adversely affecting the measurement function. Another object is the provision of level sensing without flow of current to avoid electrolysis, electrode dissolution, and the like.

Other objects, advantages and details of the method and apparatus provided by this invention appear in the following detailed description of the preferred embodiments of the invention, the detailed descriptions referring to the drawings in which:

DETAILED DESCRIPTION OF THE PREFERRED EMBODIMENT

Figure 1:
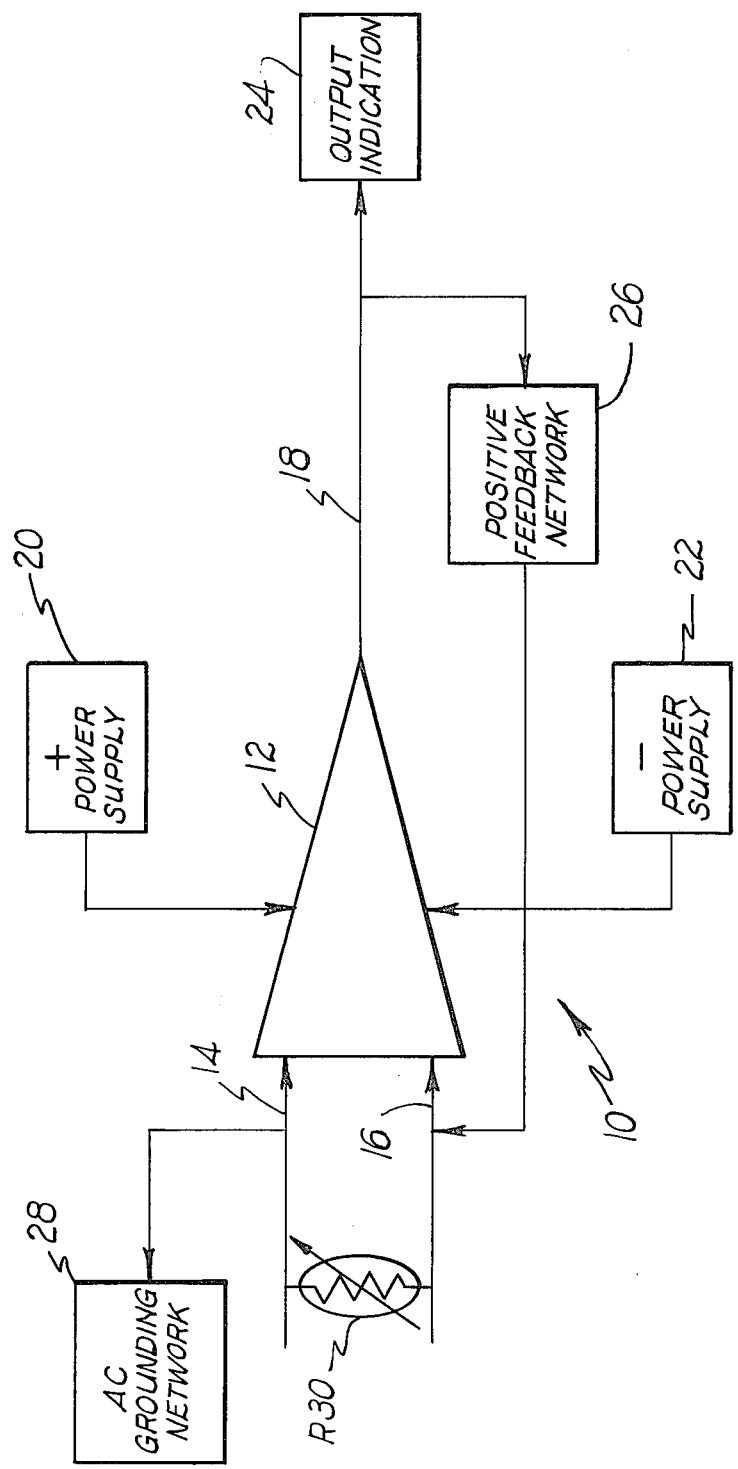
FIG. 1 is an electrical schematic block diagram of a system for monitoring the effectiveness of the corrosion inhibition characteristics of a liquid as well as sensing the presence or absence of such liquid.

Referring now to the drawings, particularly FIG. 1, a system made in accordance with the invention is identified by numeral 10 and includes a differential amplifier 12 having first and second inputs 14 and 16 and an output 18. Amplifier 12 is provided with a positive power supply 20 and a negative power supply 22. Output 18 is connected to indication means 24 and is coupled to input 16 through a positive feedback network 26. Input 14 is coupled to an a.c. grounding network 28. Coolant liquid 30 is indicated as a variable resistor connected across inputs 14 and 16.

A first electrode 32 is connected to the positive input pin 3 of differential amplifier DA1 through input line 14 and a second electrode 34 is connected to the positive input pin 3 of differential amplifier DA2 through input line 16. A negative feedback network between the amplifiers comprises a plurality of resistors R1 through R5. Resistance R2 is connected between the output 6 of amplifier DA2 and its negative input 2 and a resistance R4 connected between the output 6 of amplfer DA1 and its negative input 2. Input pin 2 of amplifier DA1 is connected to ground through resistor R5. Resistor R3 is connected between the negative input of amplifier DA2 and output 6 of amplifier DA1. Resistor R1 is connected across resistors R3 and R4. Differential amplifiers DA1, DA2 are powered by a positive power supply through pins 7 and a negative power supply through pins 4, to be explained in more detail below. The combination and specific values of resistors R1 through R5 provide negative feedback to amplifiers DA1, DA2 resulting in an output voltage, $V_o$, of approximately six times the difference between the input voltages from electrodes 32, 34. Amplifiers DA1, DA2 are both high impedance to minimize d.c. current from the electrode and avoid polarization.

Output $V_o$ is connected to the positive input pin 3 of differential amplifier DA3. The negative input pin 2 of amplifier DA3 is connected to the junction of a voltage divider connected between the positive power supply and ground comprising potentiometer R6 and resistor R7. The output pin 6 of amplifier DA3 is connected to output indication means 24 comprising a current limiting resistor R8 and serially connected light emitting diode LED1 which in turn is connected to ground. Amplifier DA3 is used as a threshold device with the particular threshold voltage at pin 2 being adjusted by potentiometer R6 so that when the voltage at pin 3 goes above that at pin 2 the amplifier produces an output thereby energizing light emitting diode LED1.

Positive power supply 20 comprises a resistor R9 connected to a d.c. power source, such as a 12 volt battery, and a zener diode Z1 connected between resistor R9 and ground. Resistor R9 and zener diode Z1 maintain the voltage at a selected level such as 6.3 volts to energize pins 7 of amplifiers DA1, DA2, DA3 as well as the voltage divider of resistors R6 and R7.

Figures 2, 2A:
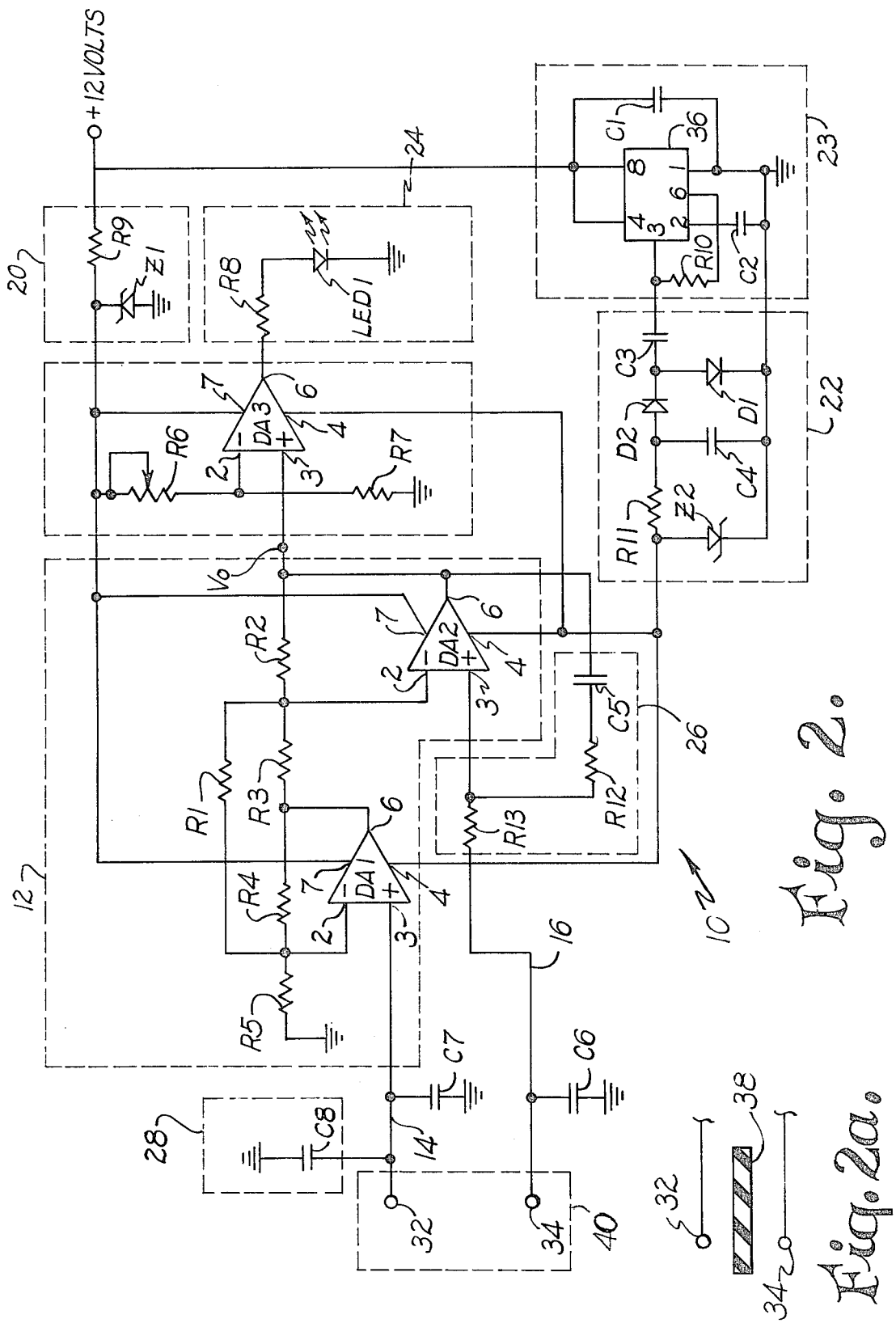
FIG. 2 depicts the FIG. 1 system in a more detailed circuit diagram.
FIG. 2a illustrates a modification of the FIG. 2 system.

Sections 22 and 23 of the FIG. 2 circuit provide the negative voltage supply for the operational amplifier from a grounded input. A negative supply with respect to ground is required since the input voltage to the operational amplifier from the electrodes may be positive or negative. Section 23 forms an oscillator and comprises a timing circuit 36 with associated resistors and capacitors. Pins 4 and 8 of timing circuit 36 are connected to the positive 12 volt d.c. source. Pin 1 of the timing circuit is connected to ground and to pins 4 and 8 through a capacitor C1. Pins 2 and 6 are connected to pin 3 through a resisotr R10 and to ground through capacitor C2.

Section 22 of the FIG. 2 circuit includes a voltage doubler arrangement of capacitors C3, C4 and diodes D1, D2. Capacitor C3 is connected to pin 3 of the timing circuit and to the anodes of diode D1 as well as the cathode of diode D2. Capacitor C4 is connected between the anode of diode D2 and ground. The cathode of diode D1 is also connected to ground. Zener diode Z2 provides negative voltage regulation at a selected level, e.g. 6.3 volts, with its cathode connected to ground and its anode connected through resistor R11 to the voltage doubler arrangement. The negative power supply is connected to pins 4 of amplifiers DA1, DA2 and DA3.

Positive feedback network 26 comprises a relatively large capacitor C5 serially connected to resistor R12 between the output and positive input pin 3 of amplifier DA2. Resistor R13 is connected to resistor R12 and pin 3 of amplifier DA2 on one side and to electrode 34 on its other side.

In order to filter out noise if desirable, small capacitors C6, C7 may be attached respectively between inputs 14, 16 and ground.

Since amplifier 12 is a differential amplifier there is a problem with getting an input on $V_{34}$ which is fed back from the output $V_o$ and an input with respect to $V_{32}$ from the output $V_o$ that is measured with respect to ground which are different from one another. If there is relatively little electrical resistance between electrodes 32 and 34 and relatively large resistance between the electrodes and ground, then the potential of the two electrodes will tend to rise and fall together preventing the amplifier from oscillating. In the present system, the voltage of electrode 34 is made to fluctuate up and down as the amplifier oscillates and this fluctuation is what is being detected. In order to prevent the electrodes from tracking one another a relatively large capacitor C8 is connected between electrode 32 and ground in order to hold the a.c. potential of electrode 32 from fluctuating and separating it in an a.c. sense from electrode 34. This is particularly useful should the radiator not be grounded or when ground is remote from the electrodes.

In some situations it may be preferred to merely decouple electrode 32 from electrode 34 as by disposing an electrically insulative barrier between the electrodes as seen in FIG. 2a where a sheet 38 of electrically insulative material is interposed between electrodes 32 and 34. Thus when the coolant liquid falls below the electrodes current must flow around the barrier to go from one electrode to another and not just along the header portion mounting the electrodes. In this case the resistance to ground would be kept small by putting the electrodes physically close thereto.

Thus, in case of capacitor C8 the system uses electrode to electrode resistance whereas in the case of barrier 38 it uses the resistance between an electrode and ground. It will be realized that level sensing could be achieved by using any two of the three different potentials of electrode 32, electrode 34 and ground.

As set forth in the above referenced patent applications, electrodes of a standard reference material, such as silver, and at least one other material, for example steel, may be employed to monitor the effectiveness of the corrosion inhibition characteristic in a coolant liquid. In the system shown in FIGS. 1 and 2 electrode 32 may be composed of steel while electrode 34 may be of silver. It will be understood that other electrodes may be used and still come within the purview of this invention. For instance, an aluminum electrode electrically connected in parallel with the steel electrode is particularly useful with aluminum radiators.

Electrodes 32 and 34 are disposed in a reservoir of a cooling system of a motor vehicle, such as radiator 40 in FIG. 2, in such a way that they are adapted to be immersed in the coolant liquid. When the inhibiting characteristic is effective a first range of electrical potential exists between the electrodes; however, when the inhibiting characteristic becomes ineffective for any reason a second range of electrical potential exists therebetween. When the potential as measured by the potential measuring circuit or amplifier 12 reaches a threshold level as it moves into the second range indicating that the corrosion inhibition is no longer effective, output indication means 24 are actuated and light emitting diode LED1 gives off a visual signal. It should be noted that in order for the system to work effectively as a corrosion sensor polarization must be avoided. Amplifier 12 is therefore, of a high impedance in order to limit current flow between the electrodes to a negligible amount.

By way of the present invention, amplifier 12, used in the corrosion sensor system as a potential measuring device, is used also as a liquid level indicator by causing the amplifier to oscillate when there is a high resistance between the electrodes. The output voltage of amplifier 12, $V_o$, is measured with respect to ground; therefore the addition of feedback network 26 results in a system which will not oscillate when the electrodes are inundated since the liquid (R30) acts as a relatively low electrical resistance but will oscillate when the electrodes are not inundated since the resistance between the electrodes then becomes high. Electrode 32 is held to a fixed potential by means of capacitor C8 so that it will not follow the a.c. potential of electrode 34; however, the d.c. potential of electrode 32, which is the corrosion sensor input voltage is unaffected. At high frequencies, where the impedances of $C_5$ and $C_8$ are negligible compared to $R_{12}$, $R_{13}$ and $R_{30}$, since there is essentially no current flow into the amplifier, the feedback voltage $V_{fb}$ due to a change in output voltage $\Delta V_o$ is approximately $$\Delta V_{fb} = (R30/R30 + R12 + R13)\Delta V_o$$

In a system made in accordance with the invention, amplifiers DA1 and DA2 used were very high gain amplifiers (CA 3140) and when combined with the resistors R1 through R5 as shown in FIG. 2, they form a single amplifier with a very high impedance, in the order of $10^{10}$ ohms and have a gain of 6.

Since $\Delta V_o = 6\Delta V_{34}$ in the forward characteristic of the amplifier, $V_{fb} = 6$ $(R30/R30 + R12 + R13)\Delta V_{34}$. As long as $V_{fb}/\Delta V_{34}$ is less than unity, a small disturbance or noise voltage will result in a smaller feedback voltage and the amplifier will be stable; when $V_{fb}/V_{34}$ becomes greater than unity it becomes unstable and will start to oscillate with a frequency approximately as follows:

$$f = 1/C5(R30 + R12 + R13)$$

Thus when electrode 34 is inundated R30 is small and the ratio $R30/R30 + R12 + R13$ is small and is less than 1/6 so there is no oscillation. In the absence of liquid the resistance between the electrodes increases by several orders of magnitude and the ratio exceeds 1/6 the amplifier functions as a relaxation oscillator.

As stated above, capacitor C5 in combination with resistances R12 and R13 determine the frequency of oscillation as well as blocking any possible d.c. current that would flow through the electrodes so therefore a high resistance capacitor is chosen to preclude any appreciable d.c. current. The value of feedback resistance R12 determines the trip point for the level sensor, that is, when the amplifier starts to oscillate. Resistance R13 is placed in series with electrode 34 to slow down the oscillation so that an observer can see light emitting diode LED1 blink. Since the impedance of the d.c. amplifier 12 is in the order of $10^{10}$ ohms the resistance has no appreciable effect in the d.c. mode; however, in the a.c. mode in effect it is in series with the resistance of the liquid R30 and thus affects the frequency of oscillation and the trip resistance.

Alternatively, rather than rely on the same light emitting diode to provide indication for the corrosion sensor as well as the level sensor the signal could be fed into a circuit sensitive to a.c. to actuate a different light. In that case the resistance R13 could be omitted resulting in a higher frequency. The specific values of the components employed in a system made in accordance with the invention are as follows:

| electrode 32 - steel | resistor R10 | 33KΩ |
|---|---|---|
| electrode 34 - silver | resistor R11 | 470Ω |
| amplifier DA1 CA3140 | capacitor C1 | .01μF |
| amplifier DA2 CA3140 | capacitor C2 | 1000 p F |
| amplifier DA3 741 | capacitor C3 | 10μF/20v |
| resistor R1 47KΩ | capacitor C4 | 22μF/15v |
| resistor R2 100KΩ | capacitor C5 | .47 pF |
| resistor R3 100KΩ | capacitor C6 | .01μF |
| resistor R4 100KΩ | capacitor C7 | .01μF |
| resistor R5 100KΩ | capacitor C8 | .47 PF |
| resistor R6 20KΩ | light emitting | |
| | LED1 diode | TIL 209A |
| resistor R7 2.2KΩ | zener diode Z1 | 6.3V |
| resistor R8 150Ω | zener diode Z2 | 6.3V |
| resistor R9 180Ω | timing circuit 36 | 555 |
| | diode D1 | 1N 4148 |
| | diode D2 | 1N 4148 |

Thus, with the above described system, if the resistance of the coolant liquid R30 is small, meaning that the electrodes are inundated, then the ratio of the appropriate resistances is small and is less than 1/6 so there is no oscillation. This of course represents normal operating conditions. When there is no oscillation the circuit has no effect on the d.c. measurement (corrosion sensor) since there are only d.c. potentials involved.

While there have been described above the principles of this invention in connection with specific apparatus, it is to be understood that this description is made by way of example and not as a limitation to the scope of the invention.

I claim:

1. A system for monitoring the corrosion inhibition characteristics of a coolant liquid and for determining whether a selected quantity of the coolant liquid is contained in a reservoir comprising
a high impedance amplifier means having first and second inputs and an output,
a first electrode adapted for immersion in the coolant liquid connected to the first input of the amplifier means,
a second electrode adapted for immersion in the coolant liquid connected to the second input of the amplifier means,
detection means connected to the output of the amplifier means for producing an output signal upon the occurrence of selected voltage conditions in the output of the amplifier means,
power supply means connected to the amplifier means and the detection means, and
a feedback network connected between the output and one of the inputs of the amplifier so that the amplifier will oscillate when there is a high resistance path between the electrodes but will not oscillate when there is a low resistance path between the electrodes, the impedance of the amplifier being sufficiently high that there is essentially no current flow between the electrodes.

2. In a circuit for a d.c. measurement having a high impedance amplifier having first and second inputs and an output, a first electrode connected to the first input and a second electrode connected to the second input, the improvement comprising a feedback network connected between at least one of the first and second inputs and the output of the amplifier so that the amplifier will oscillate when there is a high resistance path between the electrodes but will not oscillate when there is a low resistance path between the electrodes, the impedance of the amplifier being sufficiently high that there is essentially no current flow between the electrodes.

3. A circuit according to claim 2 in which the electrodes are adapted to be immersed in coolant liquid and the feedback network includes a capacitor.

4. A circuit according to claim 3 in which an electrically insulating barrier is disposed between the electrodes.

5. A circuit according to claim 3 in which one of the two inputs is connected to ground through a capacitance of a selected level so that the said one input is grounded with respect to a.c. potential but not d.c. potential.

6. A system according to claim 1 in which an electrically insulative barrier is disposed between the electrodes.

7. A system according to claim 1 in which one of the two inputs is connected to ground through a capacitance of a selected level so that the said one input is grounded with respect to a.c. potential but not d.c. potential.

8. The method of sensing the presence or absence of a conductive electrolyte on and between a pair of electrodes which are connected to a d.c. potential measuring circuit, the measuring circuit including a high impedance amplifier in order to measure the d.c. potential of the electrodes with essentially no current flow therebetween, comprising the step of using the resistance of the electrolyte between the two electrodes as part of a feedback network for the amplifier whereby in the presence of electrolyte the amplifier will not oscillate and in the absence of electrolyte the amplifier will oscillate.

9. Apparatus for sensing the presence or absence of a conductive electrolyte comprising a high impedance amplifier having first and second inputs and an output, a first electrode connected to the first input and a second electrode connected to the second input, a feedback network connected between at least one of the first and second inputs and the output of the amplifier so that the amplifier will oscillate when there is a high resistance path between the electrodes but will not oscillate when there is a low resistance path between the electrodes, the impedance of the amplifier being sufficiently high that there is essentially no current flow between the electrodes.

10. The method of sensing the presence or absence of a conductive electrolyte on and between a pair of electrodes including a high impedance amplifier, comprising the step of using the reistance of the electrolyte between the two electrodes as part of a feedback network for the amplifier whereby in the presence of electrolyte the amplifier will not oscillate and in the absence of electrolyte the amplifier will oscillate, the impedance of the amplifier being sufficiently high that there is essentially no current flow between the electrodes.

* * * * *